United States Patent

Weber et al.

[11] 4,263,310
[45] Apr. 21, 1981

[54] 8-BROMO-6-(O-CHLORO-PHENYL)-4H-S-TRIAZOLO-[3,4,-c]-THIENO-[2,3-e]-1,4-DIAZEPINES AND SALTS THEREOF

[75] Inventors: Karl H. Weber, Gau-Algesheim; Adolf Bauer, Raubling; Peter Danneberg, Ockenheim; Franz J. Kuhn, Bingen, all of Fed. Rep. of Germany

[73] Assignee: Boehringer Ingelheim GmbH, Ingelheim am Rhein, Fed. Rep. of Germany

[21] Appl. No.: 82,114

[22] Filed: Oct. 5, 1979

Related U.S. Application Data

[63] Continuation-in-part of Ser. No. 855,753, Nov. 30, 1977, Pat. No. 4,199,588, which is a continuation of Ser. No. 672,281, Mar. 31, 1976, abandoned, which is a continuation-in-part of Ser. No. 554,309, Feb. 28, 1975, abandoned.

[30] Foreign Application Priority Data

| Mar. 2, 1974 | [DE] | Fed. Rep. of Germany | 2410030 |
| Jul. 20, 1974 | [DE] | Fed. Rep. of Germany | 2435041 |
| Sep. 24, 1974 | [DE] | Fed. Rep. of Germany | 2445430 |
| Dec. 21, 1974 | [DE] | Fed. Rep. of Germany | 2460776 |

[51] Int. Cl.³ .................... A61K 31/55; C07D 495/12
[52] U.S. Cl. .................. 424/269; 260/245.5; 260/243.3; 424/232; 424/253
[58] Field of Search ............ 424/269; 260/245.5, 260/243.3

[56] References Cited

U.S. PATENT DOCUMENTS

| 3,709,898 | 1/1973 | Hester | 260/245.5 |
| 3,709,899 | 1/1973 | Hester | 260/245.5 |
| 3,904,641 | 9/1975 | Nakanishi et al. | 260/245.5 |
| 4,155,913 | 5/1979 | Hellerbach et al. | 260/245.5 |

FOREIGN PATENT DOCUMENTS 2242918  3/1973  Fed. Rep. of Germany ........ 260/245.5

Primary Examiner—Alton D. Hollins
Attorney, Agent, or Firm—Hammond & Littell, Weissenberger & Muserlian

[57] ABSTRACT

Compounds of the formula

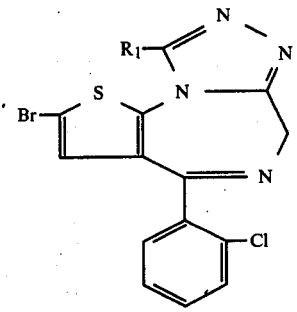

wherein $R_1$ is chlorine, bromine, cyclopropyl or cyclohexyl and non-toxic, pharmacologically acceptable acid addition salts thereof; the compounds as well as their salts are useful as tranquilizers, muscle-relaxants and anticonvulsants.

3 Claims, No Drawings

8-BROMO-6-(O-CHLORO-PHENYL)-4H-S-TRIAZOLO-[3,4,-C]-THIENO-[2,3-E]-1,4-DIAZEPINES AND SALTS THEREOF

This is a continuation-in-part of copending application Ser. No. 855,753 filed Nov. 30, 1977, now U.S. Pat. No. 4,199,588 granted Apr. 22, 1980; which in turn is a continuation of application Ser. No. 672,281 filed Mar. 31, 1976, now abandoned; which in turn is a continuation-in-part of application Ser. No. 554,309 filed Feb. 28, 1975, now abandoned.

This invention relates to a novel 8-bromo-6-(o-chlorophenyl)-4H-s-triazolo-[3,4-c]-thieno-[2,3-e]1,4-diazepines and non-toxic acid addition salts thereof, as well as to methods of preparing these compounds, pharmaceutical compositions containing them as active ingredients, and methods of using them as tranquilizers, muscle-relaxants and anticonvulsants.

More particularly, the present application relates to a novel class of compounds represented by the formula

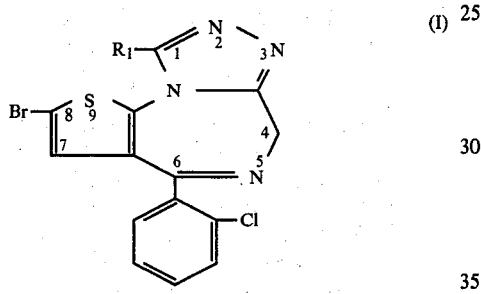

(I)

wherein $R_1$ is chlorine bromine, cyclopropyl or cyclohexyl and non-toxic, pharmacologically acceptable acid addition salts thereof.

The compounds embraced by formula I above may be prepared by the following methods:

Method A

For the preparation of a compound of the formula I wherein $R_1$ has the meanings defined above except chlorine and bromine, (a) by reacting a compound of the formula

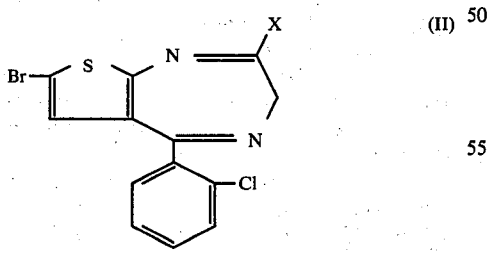

(II)

wherein X is SH—, NH$_2$—, lower alkoxy, lower alkylmercapto- or halogen, with a compound of the formula $T_1'$—CO—NH—NH$_2$      (III)

wherein $R_1'$ has the meanings of $R_1$ except chlorine and bromine; or (b) by reacting the compound of the formula

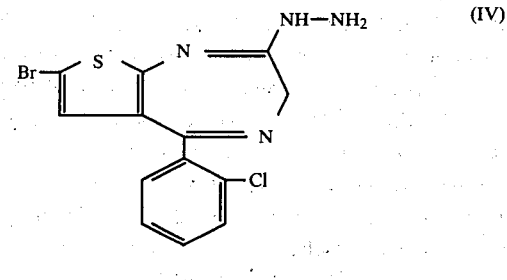

(IV)

with an acid of the formula $R_1'$—COOH      (V)

wherein $R_1'$ has the meanings defined above, or with a functional derivative of this acid.

Method B

For the preparation of a compound of the formula I wherein $R_1$ is chlorine or bromine, by chlorinating resp. brominating the compound of the formula

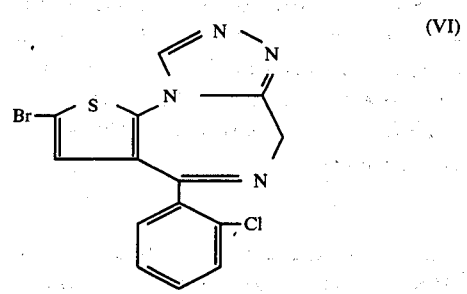

(VI)

The reaction described under method A (a) may be carried out at temperatures between 100° and 250° C. without a solvent as well as with a solvent, such as methanol, ethanol, dioxane, chloroform, tetrahydrofuran, benzene, toluene, xylene or mixtures of any two or more of these, and in the presence or absence of an acid catalyst, such as hydrochloric acid, sulfuric acid, phosphoric acid, polyphosphoric acid, acetic acid, propionic acid, benzenesulfonic acid or toluene-sulfonic acid; it is generally allowed to proceed to the end product without isolating the intermediate product of the formula

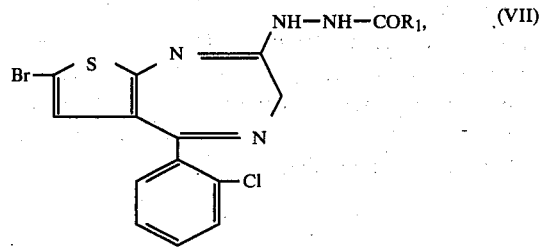

(VII)

wherein $R_1'$ has the meanings previously defined, but under milder reaction conditions (e.g. at room temperature) it is possible to isolate the intermediate product without difficulties.

The reaction described under method A (b) proceeds with the free acid of formula V or with a suitable functional derivative of this acid. Examples of suitable functional derivatives of the acid of the formula V are an orthoester or the formula $R_1'$-C(OR')$_3$; an iminoether of the formula $R_1'$—C(=NH)—OR'; an amidine of the formula $R_1'$—C(=NH)—NH$_2$; an amide of the formula $R_1'$—CONH$_2$; a thioamide of the formula $R_1'$—CSNH$_2$; an ester of the formula $R_1'$—COOR″ (for example, a methyl, ethyl or nitrophenyl ester); an acid anhydride of the formula ($R_1'$—CO)$_2$O; an acid halide of the formula $R_1'$—COHal; or a nitrile of the formula $R_1'$—CN; in these formulas $R_1'$ has the meanings previously defined, R′ is lower alkyl, and R″ is aliphatic, araliphatic or aromatic hydrocarbyl. The iminoethers and amidines are used in the form of their salts formed with mineral acids, e.g. as their chlorohydrates, as conventional.

The reaction conditions may be chosen pursuant to the particular acid derivative which is used. Generally, the reaction may be carried out without a solvent or with a solvent, such as in methanol, ethanol, chloroform, tetrahydrofuran, benzene, toluene or mixtures of any two or more of these, without or in the presence of an acid catalyst, such as hydrochloric acid, sulfuric acid, phosphoric acid, polyphosphoric acid, acetic acid, propionic acid, benzene-sulfonic acid or toluenesulfonic acid. The presence of a base, such as 2-methylimidazole, as catalyst is useful as well. The reaction temperature lies between 0° and 300° C., preferably 20° to 180° C.

The following further describe the particular variants of this method:

Variant I

In this case the functional derivative of the acid of the formula V is an orthoester of the formula $R_1'$—C(OR′)$_3$ where $R_1'$ and R′ have the meanings defined above. Usually, the reaction proceeds in the presence of an excess of the orthoester which serves simultaneously as the solvent medium, at temperatures between 90° and 100° C.; or one of the aforementioned solvents, optionally in the presence of one of the aforementioned catalysts, at temperatures between room temperature and the reflux temperature of the reaction mixture.

Variant II

In this case the functional derivative of the acid of the formula V is an iminoether of the formula $R_1'$—C(=NH)—OR′, where $R_1'$ and R′ have the previously defined meanings. It is advantageous to perform the reaction in one of the previously mentioned solvents at a temperature between room temperature and the reflux temperature of the reaction mixture.

Variant III

In this case of the functional derivative of acid of the formula V is an amidine of the formula $R_1'$—C(=NH)—NH$_2$, where $R_1'$ has the meaning previously defined. It is advantageous to perform reaction in the presence of a basic catalyst, such as a 2-methylimidazole, at elevated temperatures, for example between 150° and 250° C. In case the reaction temperature is lower, for example if the reaction is carried out at room temperature, an intermediate product of the formula

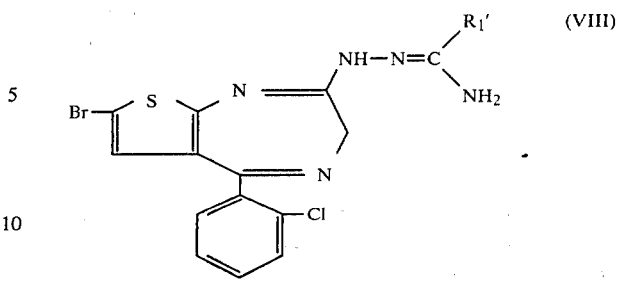

where $R_1'$ has the previously defined meaning, is first formed. This intermediate product may be isolated and subsequently subjected to a cyclization reaction by heating it at 150° to 250° C. However, isolation is not required by any means.

Variant IV

In this case the functional derivative of the acid of the formula V is an amide or thioamide of the formula $R_1'$—CONH$_2$ or $R_1'$—CSNH$_2$, where $R_1'$ has the meanings defined above. The reaction may be performed with or without a solvent, and without or with catalyst, at temperatures between 0° and 300° C.

Variant V

Here the functional derivative of acid of the formula V is an ester of the formula $R_1'$—COOR″, an anhydride of the formula ($R_1'$CO)$_2$O, an acid halide of the formula $R_1'$—COCl, or a nitrile of the formula $R_1'$—CN, where $R_1'$ and R″ have the previously defined meanings. At first, the intermediate product of the formula VII is formed, which is then cyclized as indicated under method A(a).

For the preparation of those end products of the formula I, wherein $R_1$ is chlorine or borime, pursuant to method B, the compound of the formula VI is chlorinated resp. brominated. The chlorination resp. bromination is effected in a solvent, such as carbon tetrachloride, chloroform, methylenechloride, dioxane, tetrahydrofuran, dimethylformamide or a suitable hydrocarbon, optionally in the presence of a tertiary organic base, such as pyridine, or else by means of N-chloro- or N-bromosuccinimide or elementary chlorine or bromine. The temperature of the reaction mixture, depending upon the starting material used and the method applied, lies between room temperature and the reflux temperature of the reaction mixture.

The end products of the formula I, form acid addition salts with inorganic or organic acids. Examples of non-toxic, pharmacologically acceptable acid addition salts are those formed with hydrohalic acids, sulfuric acid, phosphoric acid, nitric acid, cyclohexylsulfaminic acid, citric acid, tartaric acid, ascorbic acid, maleic acid, formic acid, salicyclic acid, methane- or toluene-sulfonic acid, 8-chlorotheopylline or the like.

The starting compounds of the formulas III and V are described in the literature, and the preparation of the compounds of the formulas VI, VII and VIII is described above.

The hydrazine derivatives of the formula IV may be prepared by reacting a compound of the formula II with hydrazine. This reaction may be performed in one of the above-mentioned solvents and, if desired, in the presence of one of the previously mentioned acid catalysts, advantageously at a temperature between room temperature and the reflux temperature of the reaction mixture.

The compounds of the formula II which may be reacted either directly with compounds of the formula III to form compounds of the formula I, or else may be reacted with hydrazine to form the compound of the formula IV, are prepared starting from the known (see German Offenlegungsschrift No. 2,217,157) compound of the formula

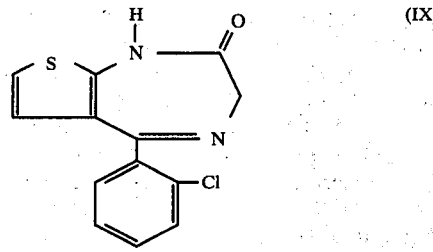

by brominating it in conventional manner, and reacting the resulting compound of the formula

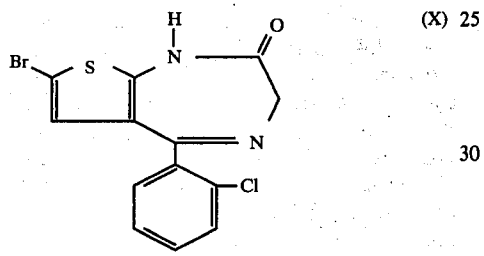

(which is also known from German Offenlegungsschrift No. 2,221,623), in a solvent, such as pyridine, dimethylformamide or tetrahydrofuran or mixtures thereof. The reaction temperature may lie between room temperature and the reflux temperature of the rection mixture. In this manner the compound of the formula II wherein X is —SH is obtained. It exists in tautomeric equilibrium with the corresponding thiono compound, as follows:

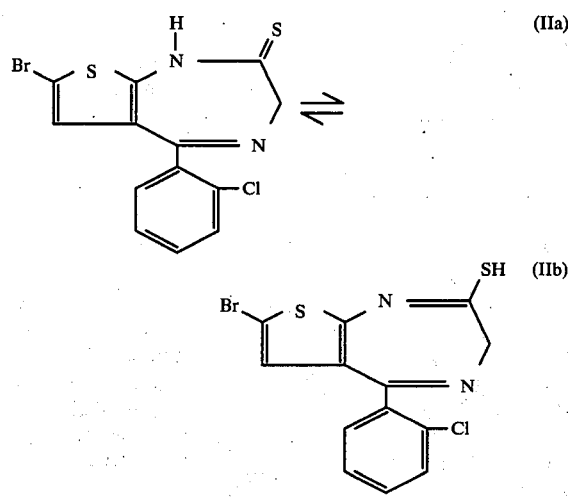

This compound may, after it has been converted into the corresponding salt by reaction with a metallizing agent such as sodium methylate or sodium amide in a solvent, be reacted without previous isolation with alkylating agents, such as methyl iodide or another lower alkyl iodide to form those compounds of the formula II wherein X is lower alkylthio.

The compounds if the formulas IX and X may be obtained pursuant to the methods of German Offenlegungsschrift Nos. 2,107,356 and 2,144,105, namely by subjecting compounds of the formula

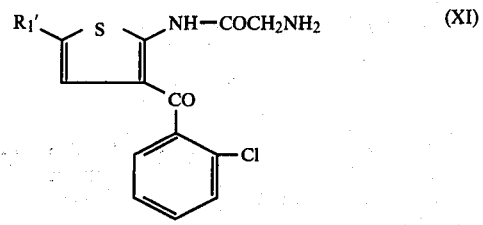

wherein $R_1'$ is hydrogen or bromine, to intramolecular condensation. An especially advantageous variant of this reaction consists of effecting the cyclization by boiling in toluene in a vessel provided with a water trap, using silicagel as the dehydrating agent. In this manner significantly higher yields and purer products are obtained.

Compounds of the formula II, wherein x is lower alkoxy, may be obtained by reacting the known aminoketone of the formula

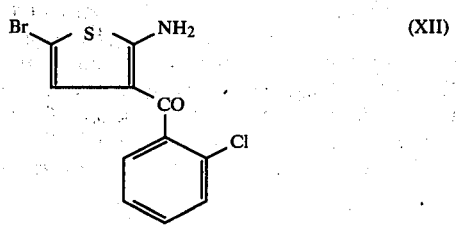

with a halo-orthoacetate of the formula $$(R'O)_3—C—CH_2Hal \qquad (XIII)$$

wherein R' has the previously defined meanings and Hal is chlorine, bromine or iodine, to form a compound of the formula

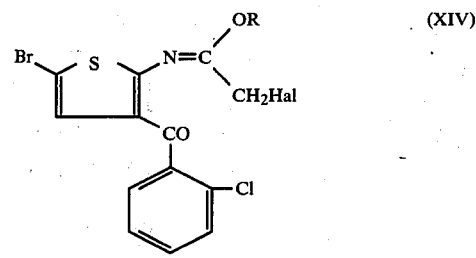

wherein R, and Hal have the previously defined meanings. In those instances where Hal is chlorine, it is advantageous first to exchange the aliphatically bonded chlorine atom in the compound of the formula XIV for iodine by means of the Finkelstein Reaction, for example by reacting it with sodium iodide in acetone. Then, the iodo-substituted compound thus obtained is reacted with ammonia in dioxane or tetrahydrofuran. In this manner, an intermediate amino compound of the formula

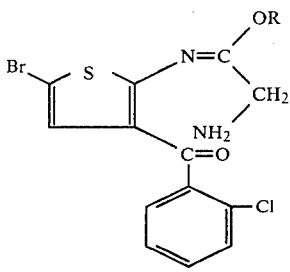

wherein R, has the previously defined meanings, is formed which, however, cyclizes spontaneously into a compound of the formula

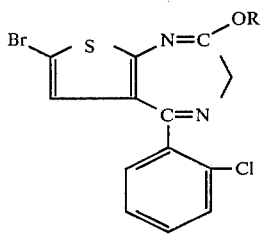

wherein R, has the previously defined meanings.

The compound of the formula II, wherein X is amino, may be prepared by reacting the compound of the formula X, which was obtained by halogenation of the compound of the formula IX, with ammonia. The reaction is advantageously performed in a solvent, such as tetrahydrofuran, and in the presence of a Lewis acid, such as titanium chloride, for example.

This compound also exists in tautomeric equilibrium as follows:

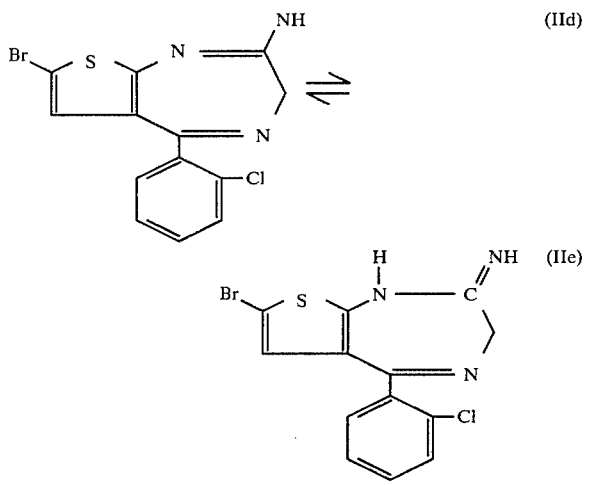

The following examples illustrate the present invention and will enable others skilled in the art to understand it more completely. It should be understood, however, that the invention is not limited solely to the particular examples given below.

EXAMPLE 1

1,8-Dibromo-6-(o-chloro-phenyl)-4H-s-triazolo-[3,4c]-thieno-[2,3e]-1,4-diazepine (a) 10 gm of 8-bromo-6-(o-chloro-phenyl)-4H-s-triazolo[3,4c]-thieno-[2,3e]-1,4-diazepine were dissolved in a mixture of 20 ml of pyridine and 100 ml of methylenechloride, and the solution was heated for 7 hours. Thereafter, a solution of 6.3 gm of bromine in 25 ml of methylenechloride was added within 5 minutes, and the mixture was refluxed for another 3 hours. Subsequently, the reaction mixture was cooled, diluted with methylene chloride and extracted twice with 1N hydrochloric acid and once with water. After drying, the methylene chloride phase was evaporated, and the residue recrystallized from ethanol. 7.0 gm (60% of theory) of the compound named in the heading, m.p. 210°–211° C., were obtained.

(b) the starting compound was obtained as follows: 27 gm of 7 bromo-5-(o-chloro-phenyl)-2-hydrazino-3H-[2,3e]-thieno-1,4-diazepine, m.p. ~300° C. (decomp.), were refluxed in a mixture of 23 ml of orthoformate and 300 ml of ethanol for 30 minutes. The solvent was evaporated, and the residue was triturated with ether. Yield: 26 gm; m.p. 214°–216° C.

EXAMPLE 2

8-Bromo-6-(o-chloro-phenyl)-1-cyclohexyl-4H-s-triazolo-[3,4c]-thieno-[2,3e]-1,4-diazepine (a) 3.7 gm of 7 bromo-5-(o-chloro-phenyl)-3H-[2,3e]-thieno-1,4-diazepine-2-thione were dissolved in 40 ml of dioxane, and the solution was refluxed with 4 gm of cyclohexane-carboxylic acid hydrazide for 30 minutes. After evaporation of the solvent, the crystalline residue was treated with ether; 4.8 gm of 7-bromo-5-(o-chloro-phenyl)-2-(cyclohexyl-carbonyl-hydrazino)-3H-[2,3e]-thieno-1,4-diazepine, m.p. 140° C. (decomp.), were obtained.

(b) A mixture of 4.8 gm of hydrazino compound thus obtained with 150 ml of toluene and 25 gm of $SiO_2$ was heated at the boiling point for 3 hours in a vessel equipped with a water trap. Subsequently, the insoluble matter was removed by suction filtration, and the reaction product was eluted with methanol from silicagel. 1.6 gm (35% of theory) of the compound names in the heading, m.p. 179°–180° C., were obtained.

Using the above-described methods, the following additional compounds of the formula I were prepared:

| Example No. | $R_1$ | $R_2$ | $R_3$ | M.P. °C. | M.P. of corresponding hydrazide of the formula VII, °C. |
|---|---|---|---|---|---|
| 3 | Br | Cl | ◁ | 212–213 | 236 (decomp.) |
| 4 | Br | Cl | Cl | 161–164 | |

The compounds of this invention, that is, those embraced by formula I above and their non-toxic, pharmacologically acceptable acid addition salts, have useful pharmacodynamic properties. More particularly, they exhibit anxiety-relieving (anxiolytic), tension-relieving, muscle-relaxing and very effective anticonvulsive activities in warm-blooded animals, such as mice and rats. They also increase the food-intake in mammals. The compounds of this invention, moreover, are characterized by extraordinarily low toxicity.

For pharmaceutical purposes the compounds according to the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.0038 to 0.10 mgm/kg body weight, preferably 0.005 to 0.05 mgm/kg body weight (oral). The daily dose rate is 0.0174 to 0.30 mgm/kg body weight.

The following examples illustrate a few pharmaceutical dosage unit compositions comprising a compound of the present invention as an active ingredient and represent the best modes contemplated of putting the invention into practical use. The parts are parts by weight, unless otherwise specified.

EXAMPLE 4

Tablets

The tablet composition is compounded from the following ingredients:

| | |
|---|---|
| 8-Bromo-6-(o-chloro-phenyl)-1-cyclohexyl-4H-s-triazolo-[3,4c]-thieno-[2,3e]-1,4-diazepine | 0.5 parts |
| Lactose | 50.0 parts |
| Corn Starch | 43.5 parts |
| Soluble starch | 5.0 parts |
| Magnesium stearate | parts |
| Total | 100.0 parts |

Preparation:

The triazolo-thieno-diazepine compound and the magnesium stearate are admixed with each other, the mixture is moistened with an aqueous solution of the soluble starch, the moist mass is granulated through a 1 mm-mesh screen, the granulate is dried and again passed through the screen, and the dry granulate is intimately admixed with the lactose and the corn starch. The resulting composition is compressed into 100 mgm-tablets, each of which contains 0.5 mgm of the triazolo-thieno-diazepine compound and is an oral dosage unit composition with effective anxiolytic, tension-relieving, muscle-relaxing and anticonvulsive action.

EXAMPLE 5

Coated pills

The pill core composition is compounded from the following ingredients:

| | |
|---|---|
| 8-Bromo-6-(o-chloro-phenyl)-1-cyclopropyl-4H-s-triazolo-[3,4c]-thieno-[2,3e]-1,4-diazepine | 1.0 parts |
| Lactose | 28.5 parts |
| Corn starch | 19.0 parts |
| Gelatin | 1.0 parts |
| Magnesium stearate | parts |
| Total | 50.0 parts |

Preparation:

The triazolo-thieno-diazepine compound, the lactose and the corn starch are intimately admixed with each other, the mixture is granulated through a 1 mm-mesh screen with the aid of an aqueous 10% solution of the gelatin, the granulate is dried and again passed through the screen, and the dry granulate is admixed with the magnesium stearate. The resulting composition is compressed into 50 mgm-pill cores which are subsequently coated with a thin shell consisting essentially of a mixture of sugar, titanium dioxide, talcum and gum arabic, and finally polished with beeswax. Each coated pill contains 1 mgm of the triazolo-thieno-diazepine compound and is an oral dosage unit composition with effective anxiolytic, tension-relieving, mescle-relaxing and anit-convulsive action.

EXAMPLE 6

Suppositories

The suppository composition is compounded from the following ingredients:

| | |
|---|---|
| 1,8-Dibromo-6-(o-chloro-phenyl)-4H-s-triazolo-[3,4c]-thieno-[2,3e]-1,4-diazepine | 5.0 parts |
| Suppository base (e.g. cocoa butter) | parts |
| Total | 1700.0 parts |

Preparation:

The suppository base is melted and cooled to 40° C., the finely pulverized triazolo-thieno-diazepine compound is stirred into the suppository base with the aid of an immersion homogenizer, and 1700 mgm-portions of the resulting mixture at 35° C. are poured into cooled suppository molds and allowed to harden therein. Each suppository contains 5 mgm of the thiazolo-thieno-diazepine compound and is a rectal dosage unit composition with effective anxiolytic, tension-relieving, muscle-relaxing and anticonvulsive action.

The amount of active ingredient in illustrative Examples 4–6 may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

What is claimed is:

1. 6-(o-Chloro-phenyl)-1,8-dibromo-4H-s-triazolo-[3,4c]thieno[2,3-e]-1,4-diazepine or a non-toxic, pharmacologically acceptable acid addition salt thereof.

2. A pharmacetucal dosage unit composition consisting essentially of an inert pharmaceutical carrier and an effective anxiolytic, tension-relieving, muscle-relaxing or anticonvulsive amount of a compound of claim 1.

3. The method of relieving anxiety, relieving tension, relaxing the muscles or suppressing convulsions in a warm-blooded animal, which comprises perorally, parenterally or rectally administering to said animal an effective anxiolytic, tension-relieving, muscle-relaxing or anticonvulsive amount of a compound of claim 1.

* * * * *

UNITED STATES PATENT AND TRADEMARK OFFICE
CERTIFICATE OF CORRECTION

PATENT NO. : 4,263,310
DATED : April 21, 1981
INVENTOR(S) : KARL H. WEBER ET AL.

It is certified that error appears in the above—identified patent and that said Letters Patent is hereby corrected as shown below:

Column 3, lines 48 and 53: "(=N-" should read -- (=NH)- --.

lines 49 and 54: Delete "H)-"

Column 6, line 3: "if" should read -- of --.

Column 8, line 40: "names" should read -- named --.

Column 9, line 26: Please correct this line to read "Magnesium stearate    1.0 parts".

line 54: Please correct this line to read "Magnesium stearate    0.5 parts"

Column 10, line 10: "mescle-relaxing" should read -- muscle-relaxing --.

line 11: "anit-convulsive" should read -- anti-convulsive --.

UNITED STATES PATENT AND TRADEMARK OFFICE
CERTIFICATE OF CORRECTION

PATENT NO. : 4,263,310
DATED : April 21, 1981
INVENTOR(S) : KARL H. WEBER ET AL.

It is certified that error appears in the above—identified patent and that said Letters Patent is hereby corrected as shown below:

Column 10, line 22:   Please correct this line to read:

" Suppository base (e.g. cocoa butter)     1695.0 parts ".

Signed and Sealed this

Twenty-first Day of July 1981

[SEAL]

Attest:

GERALD J. MOSSINGHOFF

Attesting Officer     Commissioner of Patents and Trademarks